(12) United States Patent
Childs et al.

(10) Patent No.: US 9,296,500 B2
(45) Date of Patent: Mar. 29, 2016

(54) SELECTIVE ACCESS TO CRYOPRESERVED SAMPLES

(71) Applicant: THE UNITED STATES OF AMERICA, AS REPRESENTED BY THE SECRETARY OF, DEPARTMENT OF, Washington, DC (US)

(72) Inventors: Richard W. Childs, Bethesda, MD (US); Herb Cullis, Gaithersburg, MD (US); Sumithira Vasu, Bethesda, MD (US); Phillippe Jean Broussard, Finksburg, MD (US); Kevin Douglas Clark, Gaithersburg, MD (US); Eric Kelsey Harting, Rockville, MD (US)

(73) Assignee: The United States of America, as represented by the Secretary, Department of Health and Human Services of the Office of Technology Transfer, National Institutes of Health, Washington, DC (US)

( * ) Notice: Subject to any disclaimer, the term of this patent is extended or adjusted under 35 U.S.C. 154(b) by 29 days.

(21) Appl. No.: 14/305,578

(22) Filed: Jun. 16, 2014

(65) Prior Publication Data

US 2014/0290183 A1    Oct. 2, 2014

Related U.S. Application Data

(62) Division of application No. 13/318,122, filed as application No. PCT/US2010/033575 on May 4, 2010, now Pat. No. 8,790,597.

(60) Provisional application No. 61/175,131, filed on May 4, 2009.

(51) Int. Cl.
*A61B 10/00* (2006.01)
*B65B 17/00* (2006.01)
(Continued)

(52) U.S. Cl.
CPC .............. *B65B 17/00* (2013.01); *A01N 1/0252* (2013.01); *A01N 1/0257* (2013.01);
(Continued)

(58) Field of Classification Search
CPC ................................. B29C 65/00; B01L 10/00
See application file for complete search history.

(56) References Cited

U.S. PATENT DOCUMENTS

| 4,897,138 A | 1/1990 | Shaposka et al. |
| 5,339,700 A | 8/1994 | Wright et al. |

(Continued)

FOREIGN PATENT DOCUMENTS

| EP | 0 438 626 | 7/1991 |
| EP | 0 508 474 | 10/1992 |

OTHER PUBLICATIONS

International Search Report and Written Opinion for PCT/US2010/033575, mailed Aug. 18, 2010, 10 pages.

*Primary Examiner* — Jyoti Nagpaul
(74) *Attorney, Agent, or Firm* — Klarquist Sparkman, LLP

(57) ABSTRACT

Methods and apparatus for selectively accessing a portion of a sterile cryopreserved sample are disclosed. The apparatus may include a container configured to receive the cryopreserved sample and having a first portion and a second portion, a heat sink chamber surrounding the first portion of the container, and a heat source adjacent to the second portion of the container. The chamber may be configured to maintain a non-accessed portion of the sample in a cryopreserved state. The heat source may be configured to separating an accessed portion of the sample from the non-accessed portion of the sample while maintaining the viability of the accessed portion while the non-accessed portion is maintained in the cryopreserved state.

12 Claims, 7 Drawing Sheets

(51) Int. Cl.
| | |
|---|---|
| *A01N 1/02* | (2006.01) |
| *A61M 1/02* | (2006.01) |
| *B29C 65/14* | (2006.01) |
| *B29C 65/18* | (2006.01) |
| *B29C 65/78* | (2006.01) |
| *B29C 65/00* | (2006.01) |
| *G01N 1/28* | (2006.01) |
| *B29C 65/22* | (2006.01) |
| *B29C 63/18* | (2006.01) |
| *B29C 65/04* | (2006.01) |
| *B29C 65/08* | (2006.01) |
| *B29C 65/74* | (2006.01) |
| *B29C 35/08* | (2006.01) |
| *B29L 31/00* | (2006.01) |

(52) U.S. Cl.
CPC ............ *A61M 1/0281* (2013.01); *B29C 65/14* (2013.01); *B29C 65/1412* (2013.01); *B29C 65/18* (2013.01); *B29C 65/224* (2013.01); *B29C 65/7841* (2013.01); *B29C 66/0044* (2013.01); *B29C 66/024* (2013.01); *B29C 66/1122* (2013.01); *B29C 66/348* (2013.01); *B29C 66/43* (2013.01); *B29C 66/431* (2013.01); *B29C 66/4312* (2013.01); *B29C 66/53262* (2013.01); *B29C 66/7373* (2013.01); *B29C 66/8181* (2013.01); *B29C 66/81427* (2013.01); *B29C 66/8242* (2013.01); *B29C 66/8322* (2013.01); *B29C 66/91213* (2013.01); *B29C 66/91231* (2013.01); *B29C 66/91421* (2013.01); *B29C 66/92445* (2013.01); *G01N 1/286* (2013.01); *B29C 63/18* (2013.01); *B29C 65/04* (2013.01); *B29C 65/08* (2013.01); *B29C 65/743* (2013.01); *B29C 65/7443* (2013.01); *B29C 66/0242* (2013.01); *B29C 66/43121* (2013.01); *B29C 66/73921* (2013.01); *B29C 66/818* (2013.01); *B29C 66/8122* (2013.01); *B29C 66/81261* (2013.01); *B29C 66/81811* (2013.01); *B29C 66/81821* (2013.01); *B29C 66/81831* (2013.01); *B29C 66/81871* (2013.01); *B29C 66/919* (2013.01); *B29C 66/9161* (2013.01); *B29C 66/91221* (2013.01); *B29C 66/91423* (2013.01); *B29C 66/91441* (2013.01); *B29C 66/91655* (2013.01); *B29C 66/9221* (2013.01); *B29C 66/9231* (2013.01); *B29C 66/9241* (2013.01); *B29C 66/94* (2013.01); *B29C 66/949* (2013.01); *B29C 66/961* (2013.01); *B29C 2035/0822* (2013.01); *B29C 2793/0054* (2013.01); *B29L 2031/7148* (2013.01); *Y10T 83/041* (2015.04); *Y10T 83/283* (2015.04)

(56) References Cited

U.S. PATENT DOCUMENTS

| | | |
|---|---|---|
| 5,533,342 A | 7/1996 | Gordon |
| 6,032,543 A | 3/2000 | Aarthun et al. |
| 6,383,453 B1 | 5/2002 | Banauch et al. |
| 6,491,678 B1 | 12/2002 | Rubinstein et al. |
| 2007/0245764 A1 | 10/2007 | Sasaki et al. |
| 2008/0269549 A1 | 10/2008 | Taft et al. |

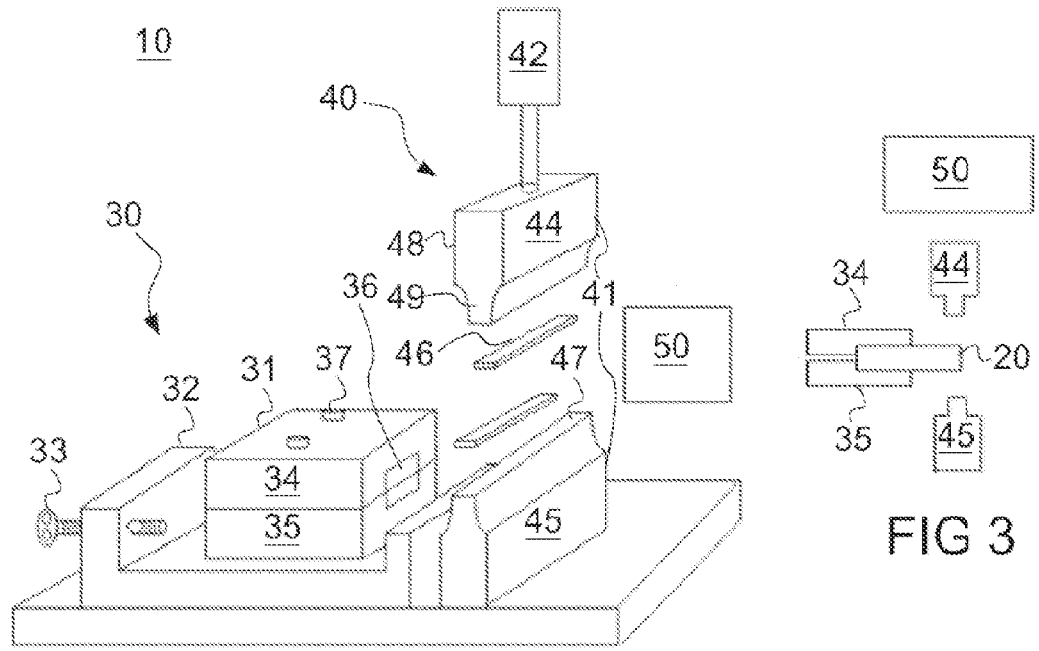
FIG 1
FIG 3
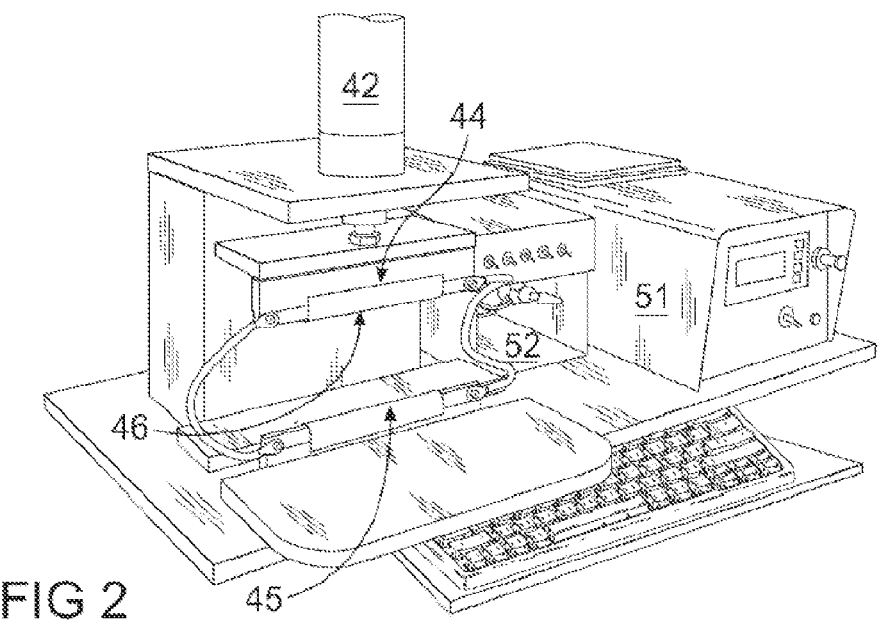
FIG 2

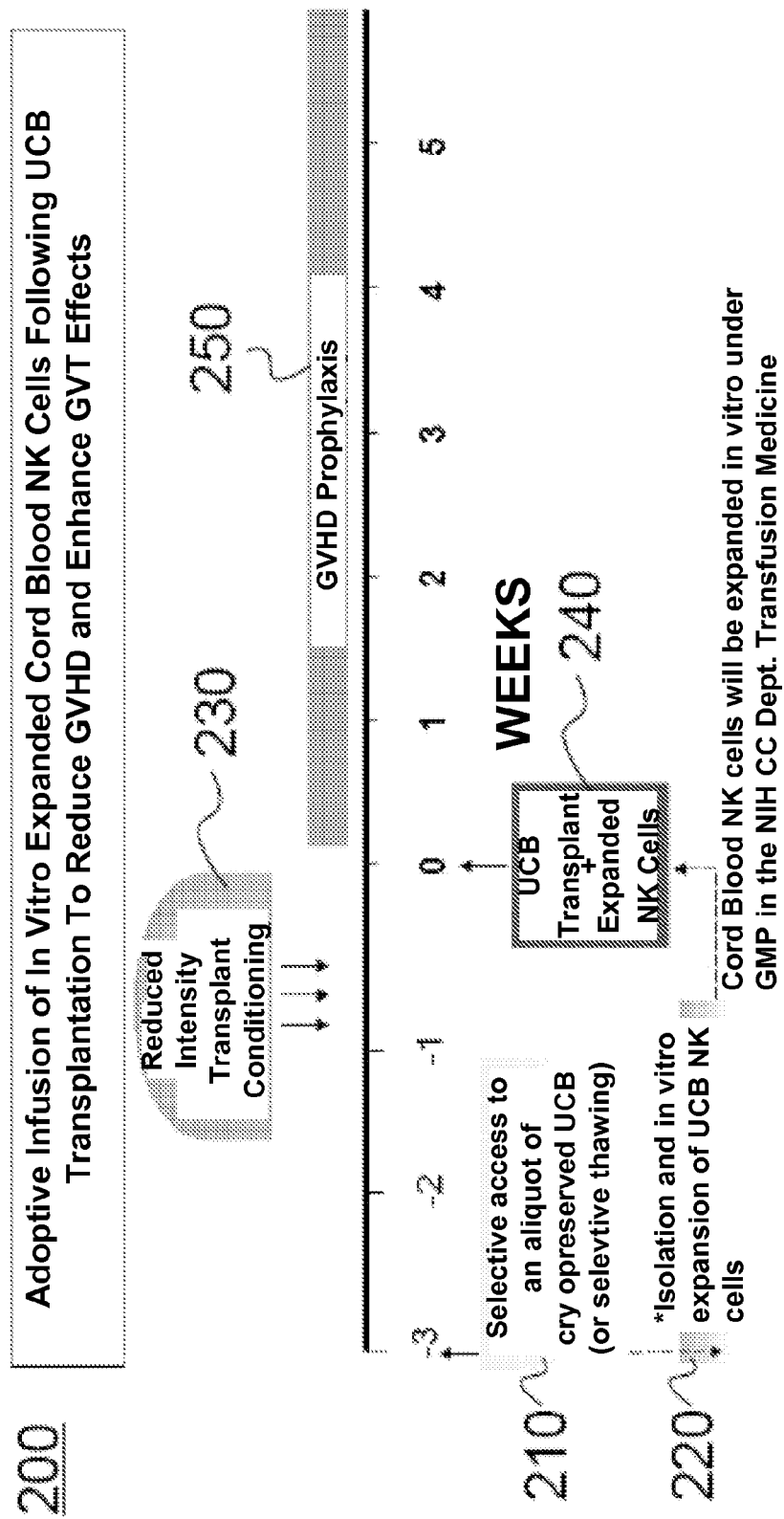

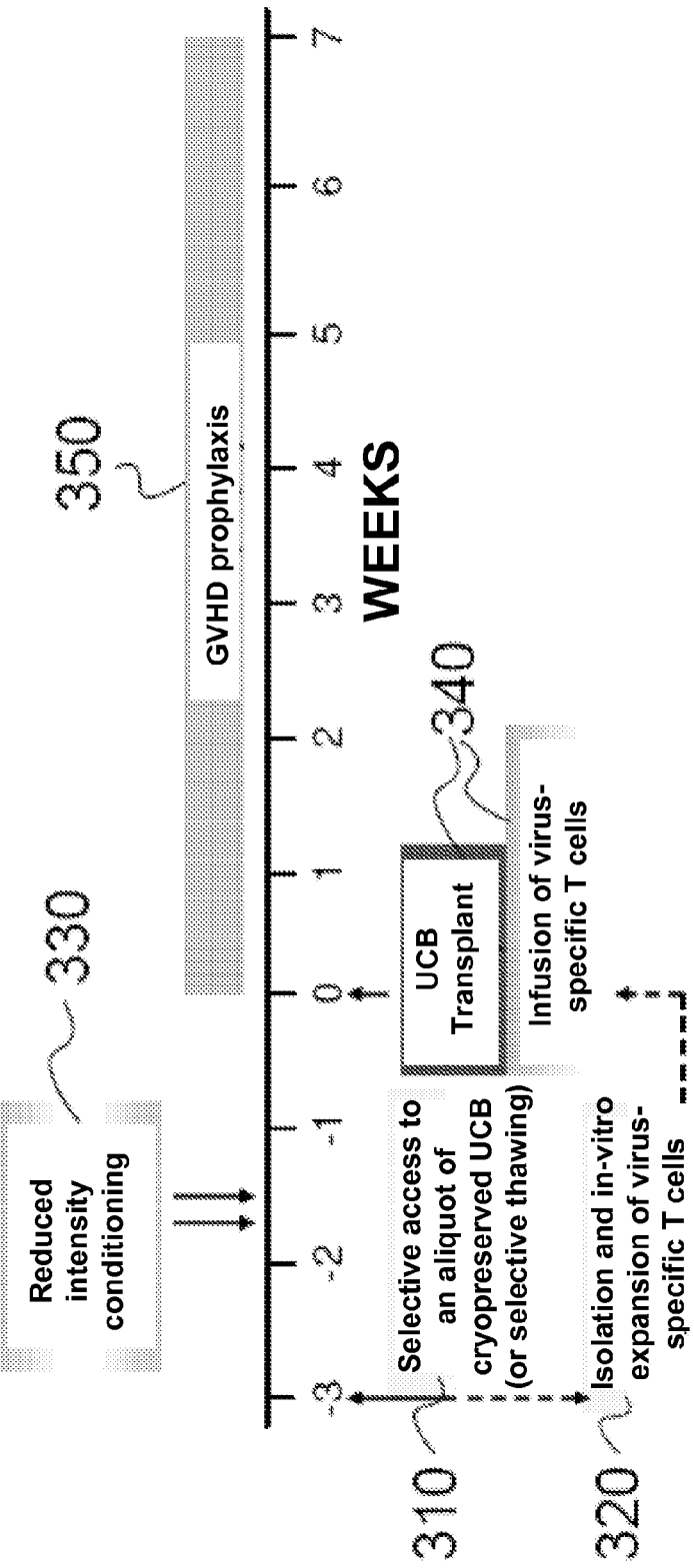

SELECTIVE ACCESS TO CRYOPRESERVED SAMPLES

CROSS-REFERENCE TO RELATED APPLICATIONS

This application is a divisional of U.S. patent application Ser. No. 13/318,122, filed Oct. 28, 2011, which is a U.S. National Stage of International Application No. PCT/US2010/033575, filed May 4, 2010, which claims the benefit of U.S. Provisional Patent Application No. 61/175,131 filed May 4, 2009.

TECHNICAL FIELD

The present invention relates to apparatus and methods for selectively accessing portions of a cryopreserved sample. The apparatus and methods provide sterile removal of portion of a sample of cryopreserved cells or other biological material while maintaining the remainder of the cryopreserved sample in a stably frozen state.

BACKGROUND

Hematopoietic stem cell sources include frozen bone marrow, mobilized hematopoietic progenitor cells, and umbilical cord blood. These stem cells can be frozen viably for subsequent thawing and transplantation for both autologous and allogeneic hematopoietic cell transplantation. About 50% of patients with diseases curable only by hematopoietic stem cell transplantation will not have a HLA-matched sibling to serve as a stem cell donor.

Matched unrelated donor transplants and transplants using umbilical cord blood (UCB) have been increasingly used as a source of hematopoietic stem cells to treat patients with hematological disorders requiring an allogeneic stem cell transplant (SCT) who lack an HLA matched sibling or unrelated donor. The advantages to UCB transplantation include the ease and rapidity of availability of the UCB unit (more than 100,000 frozen UCB units are available in public registries), the ability to effectively use a less-than-perfect HLA match, and lower rates of graft-versus-host disease (GVHD) compared to mismatched bone marrow or peripheral blood stem cell transplants. GVHD, an orphan disease, is a major obstacle to successful allogeneic stem cell transplantation. With UCB transplants, even a 4/6 or 5/6 HLA-matched donor can be used safely. Rates of GVHD with 4/6 or 5/6 matched UCB have been comparable to that of matched bone marrow transplantation. Therefore, UCB transplants appear to be an effective option for patients with disease curable by allogeneic stem cell transplant (SCT) who lack a suitable HLA-matched donor.

However, despite the reduced GVHD associated with HLA mismatching, severe GVHD resulting in morbidity and death still occurs in up to 15% of recipients of a UCB transplant. Furthermore, because the majority of T-cells contained within an UCB unit are naive to viral pathogens, severe morbidity and death associated with viral reactivation of adenovirus, cytomegalovirus, and Epstein Barr virus (EBV) occurs more commonly after UCB transplantation compared to peripheral blood or bone marrow transplants. There is a need to develop a solution to suppress the alloreactivity of infused donor T-lymphocytes to reduce the substantial GVHD-associated morbidity and mortality that occurs following UCB transplantation while simultaneously providing immune competent viral specific T-cells to prevent viral reactivation.

The use of adoptive natural killer (NK) cell infusions following UCB transplantation offers the possibility of reducing GVHD while enhancing a potent graft-versus-tumor (GVT) effect. Data suggest that the NK cells protect recipients from GVHD in the setting of killer IgG-like receptor (KIR) ligand incompatibility. In humans, this protective effect is most evident with MHC mismatched transplantation, usually following in vivo or in vitro T-cell depletion. In MHC mismatched murine transplant models, lethal GVHD is reduced following the adoptive infusion of KIR ligand mismatched NK cells. Adoptively infused NK cells, while reducing GVHD, simultaneously mediate an anti-tumor effect against tumor cells. These data support the potential for an adoptive infusion of alloreactive NK-cells to reduce the incidence of GVHD and tumor relapse in humans undergoing T-cell-replete allogeneic SCT. Furthermore, they suggest that an adoptive infusion of in vitro expanded NK cells isolated from the same UCB unit used for SCT might likewise reduce GVHD and improve survival following UCB transplantation. NK cells isolated from thawed umbilical cord blood units can be expanded in vitro by 100 to 1000 fold, numbers that would be sufficient to be used for adoptive transfer into recipients of an umbilical cord blood transplant.

Viral reactive T-cells capable of killing adenovirus, cytomegalovirus, and Epstein Barr virus (EBV) can be expanded in vitro from peripheral blood mononuclear cells (PBMC). Using dendritic cells generated from human CD34+ cells or monocytes transduced with a adenoviral vectors encoding CMV antigens, CD4+ T-cells and cytotoxic T-cells that are adenoviral and CMV reactive have been stimulated and expanded. By further stimulating these T-cells with EBV transformed B-cells, EBV-Reactive T-cells can likewise be expanded in vitro and can be used to prevent and treat EBV lympho-proliferative disorder. CD4+ T-cells and cytotoxic T-cells that are adenoviral, CMV-reactive, and EBV-reactive can be generated in vitro from mononuclkaer cells obtained from UCB units. However, this process of viral reactive T-cell expansion typically takes 6-8 weeks. Unfortunately, many life-threatening viral reactivations occur within the first 6 weeks of UCB transplantation, so expansion of viral reactive T-cells from mononuclear cells taken from a thawed UCB unit (at the time of transplantation) would not be available in time to prevent a majority of viral reactivations associated with UCB transplantation.

Furthermore, data suggest that adoptive NK cell infusions must be given early, at the same time the hematopoietic stem cells are transplanted, in order to kill host antigen presenting cells and thus prevent GVHD. With standard PBSC or marrow transplants, the donor is typically available 2-4 weeks before transplantation to donate lymphocytes to expand NK cells or to collect T-cells should a subsequent donor lymphocyte infusion be required to treat disease relapse. On the other hand, with frozen UCB units, adoptive NK cell and/or T-cell infusions at the time of transplantation are currently not possible, because the entire UCB unit is defrosted at one time and transplanted, eliminating the donor cell source from which these cells could be expanded. Although a portion of the thawed UCB unit could be set aside at the time of thawing and preserved to expand NK cells or T-cells, in vitro NK and T-cell expansions require 3-8 weeks to expand a sufficient number of cells to prevent GVHD.

There have been previous approaches to this problem by providing storage containers with separate storage compartments to allow different portions of a frozen cell sample to be thawed at different times. See, e.g., U.S. Patents and applications U.S. Pat. No. 6,491,678, 2005/0084838, and 2004/0097862, and PCT Applications 2007/059084 and 97/49959.

These methods require separation of the cell sample portions before freezing. Most frozen UCB units are contained in a bag with either a single compartment or two compartments, the two compartments respectively containing, for example, 5 ml and 20 ml of frozen umbilical cord blood. For these types of UCB units, the aforementioned solutions do not permit thawing or selective access to only a small portion of the UCB unit, i.e., 1-2 ml.

Currently, no method exists that is capable of selectively accessing and/or partially thawing one portion of a frozen UCB unit without compromising the integrity, sterility, or viability of the unthawed portion, e.g., 2-4 weeks prior to a transplant, in order to expand NK cells, T-cells, or hematopoietic stem cells in vitro, for adoptive infusion at the time of transplantation of the remaining portion of the UCB unit. Such a method could allow these expanded cells (i.e. hematopoietic stem cells, NK cells, T-cells, etc.) to be used to potentiate graft-versus leukemia effects, prevent GVHD, and to prevent or treat viral infections in the post-UCB transplant period. Such a method could permit adoptive cellular immunotherapy using immune cells from the same UCB unit that is transplanted to more rapidly restore lympho-hematopoietic function. The ability to selectively thaw a portion of a UCB unit has utility in numerous other therapeutic modalities.

SUMMARY

Methods and apparatus are disclosed that can selectively access or thaw a portion or portions of a UCB unit, or other frozen cells such as frozen bone marrow or frozen mobilized hematopoietic progenitor cells, as well as non-cellular samples such as plasma or serum, in a thermoplastic container, while maintaining cold temperatures in the remainder of the un-accessed or unthawed portion to preserve its viability. The ability to successfully access or thaw a portion of a UCB unit without compromising the integrity, sterility, or viability of the unthawed portion may provide the opportunity to expand ex vivo cord blood NK cells, T-cells, or hematopoietic stem cells in advance of transplantation of the remaining portion of the same or other UCB unit or units. In vitro expanded UCB T-cells and NK cells may be adoptively infused at the time of UCB transplantation, which is expected to reduce incidence of GVHD and reduce complications associated with viral reactivation, compared to UCB transplantation alone.

In a first embodiment, the disclosed apparatus and method may employ a liquid nitrogen-cooled block enclosure that may cover a non-accessed portion of a frozen sample assembly, e.g., a UCB unit, thereby keeping that portion of the sample in a stably frozen state. The remaining accessed portion of the frozen sample may be isolated and severed from the non-accessed portion such as by using a heat and pressure source such as one that includes two tapered severing bars, each severing bar including an electronically-controlled heating element positioned at the leading edge. A compressor such as a pneumatic cylinder may be used to provide a force for the severing bars to push onto opposite sides of the plastic bag surrounding the frozen sample. The heating element and the compressor allow the severing bars to melt a small portion of the frozen phase sample, which is quickly refrozen, as the severing bars penetrate through the sample assembly. When the severing bars have penetrated through the sample assembly to within a desired distance of each other, the temperature of the heating elements and the force provided by the pneumatic cylinder may be increased, such that a seal may be formed by melting and fusing opposing portions of the plastic bag surrounding the frozen sample, thereby separating the non-accessed portion from the accessed portion.

In a second embodiment, the disclosed methods and apparatus employ deformable and compliant bladders filled with liquid nitrogen or another coolant that may cover a portion, e.g., up to 90%, of a frozen sample, e.g., a UCB unit, thereby protecting that portion from thawing. The remaining aliquot amount (e.g., 10%) of the frozen sample may be thawed using a controlled heat source, such as infrared energy. Temperature probes may be placed on the frozen and thawed portions of the sample to ensure that the frozen portion does not increase in temperature and to allow for feedback control of the infrared energy device used to selectively thaw a portion of the sample. Simultaneous mechanical pressure and infrared thermal energy may be applied to the selected aliquot portion of the frozen sample to thaw the aliquot portion and to create a seal between the frozen portion and thawed aliquot portion of the sample. A sterile bag or other vessel may be used to collect the thawed portion of the sample. Tubing leading to the bag or vessel may be heat-sealed to allow for sterile collection of the thawed portion. The frozen portion of the sample may be returned to a freezer to be potentially used during UCB transplantation.

The accessed or thawed aliquot portion of the UCB unit may be isolated, and the cells may undergo preparation causal to in vitro expansion under GMP conditions. For example, for NK cell expansions, the method taught in pending U.S. patent application Ser. No. 11/718,387 may be used. Laboratory experiments have shown that NK cells isolated from thawed umbilical cord blood units can be expanded in vitro by 100 to 1000 fold, numbers analogous to those achieved when adult NK cells are expanded in vitro.

In a third embodiment, the disclosed methods and apparatus employ a patch layer of material positioned between a container containing the cryopreserved sample and the heating elements. The patch layer can be made of plastic or any other material that melts, preferably, at around the same temperature as the container. As the patch layer melts, it welds to the container and creates a patch for any tears that can develop in the container as it is being severed by the heating elements. The patch layer can be sized similar to the heating elements so as only require enough material to perform the welding operation. Alternatively, the patch layer can be an open-ended patch-layer bag in which the container sits. In such a case, once the heating elements seal the container, the patch-layer bag is sealed so as to further contain the container in a separate closed bag.

In a fourth embodiment, a layer of heat-resistant material, such as a polymer material (e.g., polytetrafluoroethylene (PTFE), Perfluoroalkoxy (PFA), Fluorinated ethylene propylene (FEP), etc.) can be positioned between the heating elements and the patch layer. The layer of heat-resistant material (referred to as a release film) can be thin enough to allow heat transfer to the container, but has a sufficiently high melting point so as not stick to the heating elements. Thus, the release film protects the container from being pulled apart as the heating elements are moved away from the container.

The foregoing features and advantages will become more apparent from the following detailed description, which proceeds with reference to the accompanying drawings.

BRIEF DESCRIPTION OF THE DRAWINGS

The foregoing summary, as well as the following detailed description, is better understood when read in conjunction with the appended drawings. There is shown in the drawings example embodiments of various embodiments, however the present invention is not limited to the specific methods and instrumentalities disclosed. In the drawings:

FIG. 1 is a diagrammatic perspective view of an apparatus for selective access to cryopreserved samples, according to a first embodiment;

FIG. 2 is a perspective view of a severing bar control system suitable for use in the apparatus for selective access to cryopreserved samples depicted in FIG. 1;

FIG. 3 is a side perspective view of a cold block holding portion and a sample, the sample positioned between the severing bars depicted in FIG. 2;

FIG. 8A is a transplant protocol timeline of when the first embodiment apparatus for selective access of frozen cells or the second embodiment apparatus for selective thawing of frozen cells may be used, in the context of adoptive infusion of in vitro expanded cord blood NK cells; and FIG. 8B is a transplant protocol timeline of when the first embodiment apparatus for selective access of frozen cells or the second embodiment apparatus for selective thawing of frozen cells may be used, in the context of adoptive infusion of ex vivo expanded viral-reactive T lymphocyte cells.

FIG. 11B shows the severing bars of FIG. 11A bearing down on the assembly in order to seal the container and the patch-layer bag into two parts with a sealed strip there between.

DETAILED DESCRIPTION OF ILLUSTRATIVE EMBODIMENTS

Figure 4:
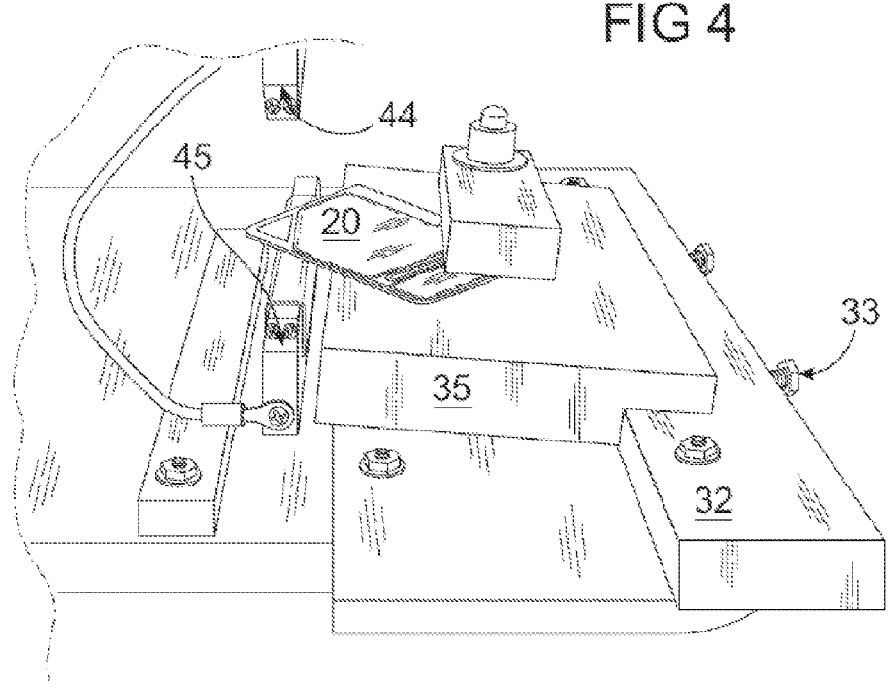
FIG. 4 is a diagrammatic side view of a frozen sample bag clamped inside of the cold block depicted in FIG. 1.

The embodiments described below provide apparatus and methods for selectively accessing portions of cryopreserved cells. The embodiments described below illustrate several aspects of the present invention and are not intended to be limiting. The embodiments can find utility in any environment where there is a need for selective accessing of portions of cryopreserved cells.

Referring to FIGS. 1-3, a first embodiment selective access system 10 includes a sample assembly 20, a cooling system 30 for maintaining (actively or passively) a non-accessed portion of the sample assembly 20 in a stably frozen state during the operation of the selective access system 10, a heat and pressure source 40 for separating and sealing off an accessed portion of the sample assembly 20 from the non-accessed portion of the sample assembly 20, and a heat and pressure control system 50 for managing the temperature and pressure of the heat and pressure source 40.

The sample assembly 20 may include umbilical cord blood, for example. The sample assembly 20 may include one or more of any other cell sample or biological material sample, including, for example, stem cells, red blood cells, white blood cells, modified cells, stromal cells, hybridoma cells, producer cells, pathogenic cells, epithelial cells, mesenchymal cells, sperm, embryos, biological cell parts, virus samples, rickettsial cells, vaccine materials, antigenic materials, cyotokines, and hormones. The sample assembly 20 may also contain plasma, serum, antibodies, lymphocytes, or any other cellular or non-cellular material. The sample assembly 20 may contain a human sample, or it may contain an animal sample, a plant sample, a synthetic sample, or any other type of frozen sample. Many such cell samples or biological material samples that are frozen with cryoprotectants form amorphous solids, rather than crystalline solids. It is believed that the relatively poor thermal conduction of cell samples or other biological material samples that are amorphously frozen (compared to materials that freeze in a crystalline state) may more easily allow for sample assemblies 20 containing these materials to be selectively accessed with the apparatus and methods described below, while only thawing a small portion (e.g., 2-5%) of the sample assembly 20.

Figure 6A:
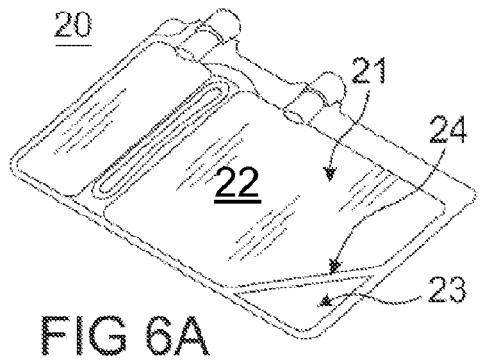
FIG. 6A is a top perspective view of the frozen sample bag depicted in FIG. 4, after a selected portion of the frozen sample has been separated from the remainder of the frozen sample.
Figure 6B:
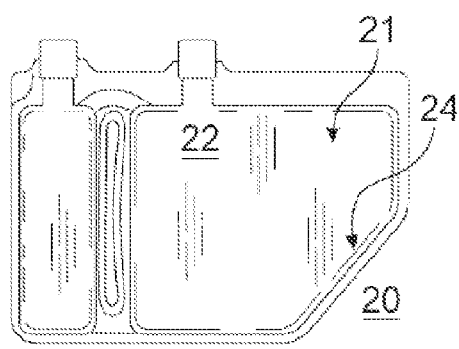
FIG. 6B is a top view of the frozen sample bag depicted in FIG. 6A, after the selected portion of the frozen sample has been removed from the remainder of the frozen sample bag.

As shown in FIGS. 3, 6A, and 6B, the sample assembly 20 may include a plastic bag 21 that initially includes a single compartment, but after the operation of creating a seal, the plastic bag is divided into two compartments, as shown in FIGS. 6A and 6B. Specifically, the two compartments include a non-accessed portion or aliquot 22 that a user intends to remain stably frozen and sterile and an accessed portion or aliquot 23 that a user may intend to remain stably frozen and sterile after the accessed portion 23 is separated from the non-accessed portion 22. A seal 24 can be produced by the severing bars 41 during operation of the selective access system 10 in order to create the two compartments. Although the plastic bag 21 is shown in FIGS. 3, 6A, and 6B as a flexible plastic bag, in other embodiments, the plastic bag 21 may be a more rigid plastic freezing tube. Plastic bag 21 may be any container capable of containing a cell sample or other biological material in a stably frozen state and capable of forming a seal 24 when sufficient heat and pressure are applied to the container. In an alternative embodiment, ultrasonic energy may be used instead of heat. For this purpose, a commercial sealer, such as one offered by the Herrmann Group, Utien Pack Company, or others may be used. It should be also noted that although the seal 24 is angled with respect to a longitudinal axis of the sample assembly, the seal can be at any desired angle including perpendicular to the longitudinal axis.

In some embodiments, the plastic bag 21 may be surrounded by an additional protective, deformable, sterile barrier or cover that may help contain any leaks or failures of the plastic bag 21 during operation of the selective access system 10. Such additional barriers may be beneficial when the plastic bag 21 has previously fractured, but the user may not find out about the fracture until operation of the selective access system 10. Such additional barriers may also be beneficial to preserve the sealing and sterility of infectious or precious cellular samples or other biological materials included in plastic bag 21 if the selective access system 10 would experience a failure or error during usage. Such additional barriers may be made out of a material (e.g., Teflon or Kapton) that can be sterilized by conventional sterilization procedures, for example, wet heat, dry heat, chemical disinfectants, e-beam irradiation, gamma irradiation, or ultraviolet light irradiation.

The cooling system 30 includes a block enclosure 31 for receiving the sample assembly 20, a block receiver 32 for supporting and positioning the block enclosure 31, and block positioning elements 33 for advancing the block enclosure 31 toward the heat and pressure source 40. The block enclosure 31 includes an upper block portion 34, a lower block portion 35, an internal cavity 36 that is sized to receive the sample assembly 20, and connecting elements 37 for coupling the block portions 34 and 35 together.

Figure 7:
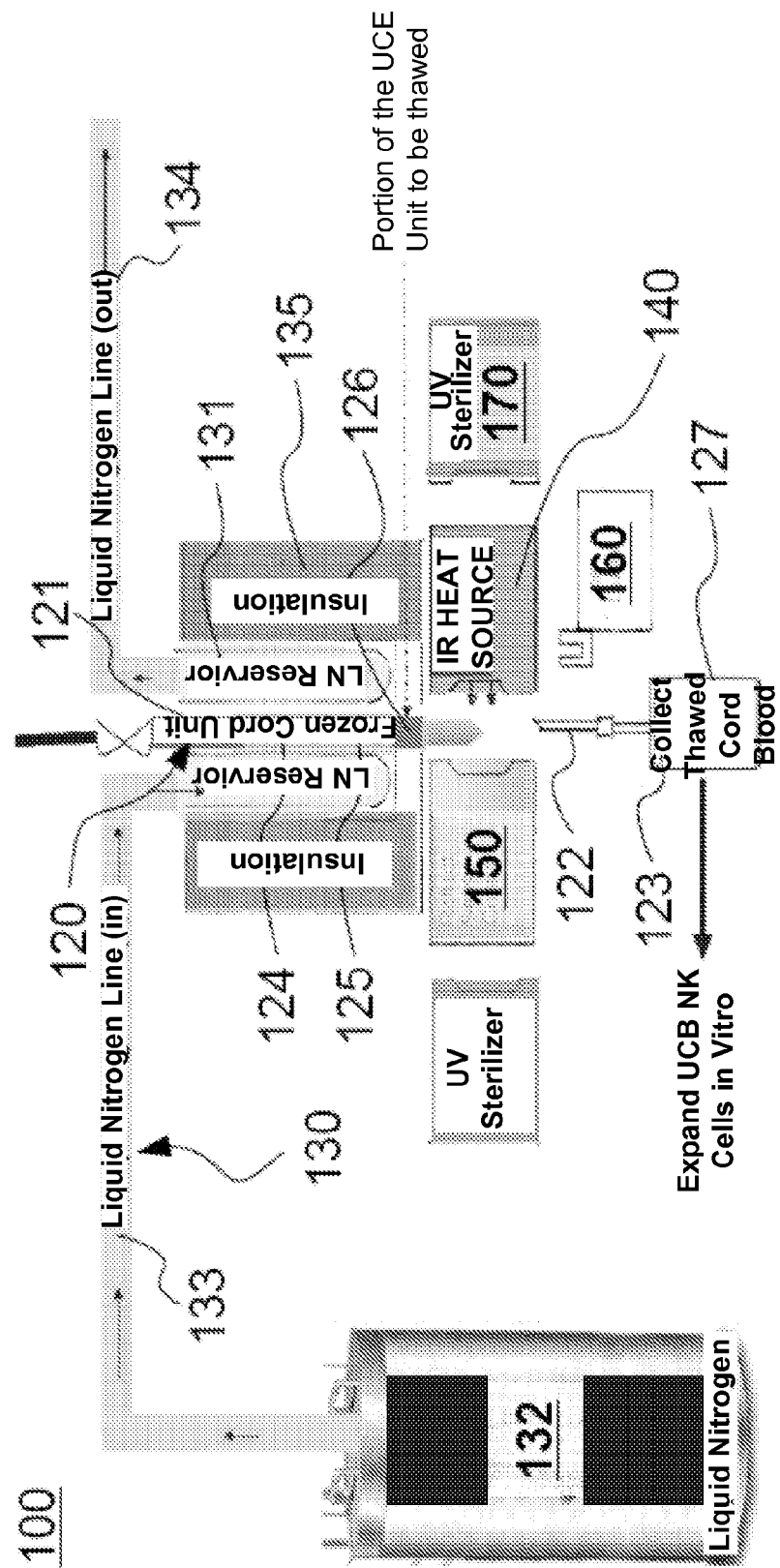
FIG. 7 is a diagrammatic view of an apparatus for selective access to cryopreserved samples, according to a second embodiment.

The cooling system 30 keeps the non-accessed portion 22 of the sample assembly 20 in a stable frozen state during the operation of the selective access system 10. As shown in FIGS. 1, 3, and 4, the cooling system 30 includes a block enclosure 31 that may have a very low temperature during the operation of the selective access system 10, for example, −196° C. In some embodiments, the cooling system 30 may take other forms. For example, as shown in FIG. 7, a cooling system 130 may include bladders filled with liquid nitrogen. In some embodiments, the cooling system 30 may be cooled with or include dry ice, which may keep the sample assembly 20 at −76° C. In other embodiments, any other coolant may be used to manage the temperature of the cooling system 30 that is capable of keeping the non-accessed portion 22 of the sample assembly 20 at a low enough temperature, e.g., below −40° C., to keep it in a stable frozen state.

In the embodiment shown in FIGS. 1, 3, and 4, the cooling system 30 passively maintains the sample assembly 20 in a cold state, due to its low temperature and greater thermal mass than the sample assembly 20, by serving as a heat sink (e.g., passively drawing away heat energy from the sample assembly 20 during the operation of the selective access system 10). In some embodiments (e.g., the second embodiment shown in FIG. 7), the cooling system 30 may actively cool the sample assembly 20, for example, by active circulation of a coolant through the cooling system 30. In some embodiments, the cooling system 30 may include a refrigeration unit capable of substantially surrounding the sample assembly 20 and keeping the non-accessed portion 22 of the sample assembly 20 in a stably frozen state. The exact configuration and components of the cooling system 30 may be chosen based on design and performance characteristics for the selective access system 10, such as the temperature and heat transfer requirements for the particular sample assembly 20.

As shown in FIG. 1, for example, the block enclosure 31 may include an internal cavity 36 that may be approximately shaped to enclose the non-accessed portion 22 of the sample assembly 20. As shown in FIG. 3, the block enclosure 31 may enclose the non-accessed portion 22 of the sample assembly 20 within the internal cavity 36, while allowing the accessed portion 23 of the sample assembly 20 to project out of the internal cavity 36 and across a vertical plane defined by the leading edges 47 of the severing bars 41. The upper block portion 34 and the lower block portion 35 of the block enclosure 31 may be hinged or flexibly connected, so that the block enclosure 31 may be opened to receive the sample assembly 20 and closed to retain the sample assembly 20. The connecting elements 37 may, for example, include screws, a latch, or any other fastening mechanism that is known in the art to keep the block enclosure 31 closed after the sample assembly 20 has been inserted into the internal cavity 36.

The block enclosure 31 may serve as a heat sink that is capable of removing heat energy from the sample assembly 20 during operation of the selective access system 10, via heat transfer. The block enclosure 31 may have a mass that is substantially greater (e.g., 10-30 times greater) than the mass of the sample assembly 20, which may allow the block enclosure 31 to maintain the temperature of the stably frozen non-accessed portion 22 of the sample assembly 20 within the desired temperature increase range (e.g., 5° C.) for the duration of the operation of the selective access system 10. For example, the sample assembly 20 may weigh 35 grams, and the block enclosure 31 may weigh 500-1000 grams.

The block enclosure 31 may be made from a material that has a relatively high thermal mass for its volume, for example, a metal material such as brass, iron, steel, or aluminum. In other embodiments, the block enclosure 31 may be made from any other material that has a relatively high thermal mass compared to the mass of the sample assembly 20. Because the block enclosure 31 has a much higher thermal mass than the sample assembly 20, any increase in the temperature of the sample assembly 20 during the operation of the selective access system 10 may be distributed throughout the block enclosure 31 and the sample assembly 20, thereby preventing the increase of temperature of the sample assembly 20 from exceeding the desired temperature increase range.

In the embodiment shown in FIGS. 1, 3, and 4, the block enclosure 31 is not coupled to a coolant during the operation of the selective access system 10. In such embodiments, the block enclosure 31 is cooled to a target temperature, for example, −196° C., by immersing the block enclosure 31 in liquid nitrogen or by placing the block enclosure 31 in a refrigerator containing liquid nitrogen prior to operation of the selective access system 10. The block enclosure 31 may be cooled to the same target temperature as the storage temperature of the sample assembly 20, for example, by storing the block enclosure 31 and the sample assembly 20 in the same refrigerator or cooling apparatus. The block enclosure 31 may be portable or capable of being manually transferred by one person from a refrigerator, for example, to the block receiver 32, after the block enclosure 31 has reached the desired temperature range.

The block receiver 32 is configured to support the block enclosure 31, and the block receiver 32 provides an anchor point to support the block positioning elements 33 so that the block positioning elements 33 can move the block enclosure 31 toward the severing bars 41 or pull the block enclosure 31 away from the severing bars 41. In an example embodiment, the block positioning elements 33 are threaded screws that penetrate through tapped holes in the block receiver 32 and are coupled to the block enclosure 31. The block receiver 32 and the block positioning elements 33 may position the block enclosure 31 such that the desired boundary between the non-accessed portion 22 of the sample assembly 20 and the accessed portion 23 of the sample assembly 20 lies in the plane defined by the severing bars 41.

During operation of the selective access system 10, as the severing bars 41 begin to separate the non-accessed portion 22 of the sample assembly 20 from the accessed portion 23 of the sample assembly 20, the block positioning elements 33 may pull the block enclosure 31 and the sample assembly 20 away from the severing bars 41. This movement of the sample assembly 20 away from the severing bars 41 may help to maintain the position of the severing bars 41 relative to a depression that may be formed in the sample assembly 20, as the plastic included in the sample assembly 20 stretches to form the depression.

As shown in FIG. 4, the lower block portion 35 may be mounted onto the block receiver 32 via a hinge or pivot, for example, near the block positioning elements 33, so that the lower block portion 35 may be angled upward or downward relative to the block receiver 32.

The upward or downward angle of the lower block portion 35 may allow the vertical position of the end of the lower block portion 35 nearest the severing bars 41 to be approximately the same as the vertical position of the leading edge 47 of the lower severing bar 45. It may be beneficial to position the end of the lower block portion 35 nearest the severing bars 41 at the same vertical height of the leading edge 47 of the lower severing bar 45, to allow the non-accessed portion 22 of the sample assembly 20 to rest on the lower block portion 35, and to allow the anticipated severing location in the sample assembly 20 to rest on the leading edge 47 of the lower severing bar 45, without creating excessive bending stress in the sample assembly 20. In some embodiments, the lower block portion 35 may be oriented at any angle relative to the block receiver 32, such that the bending stress in the sample assembly 20 may be minimized.

The heat and pressure source 40 includes severing bars 41 and a compressor 42 for providing pressure to the severing bars 41. The severing bars 41 include an upper severing bar 44 and a lower severing bar 45, the bars 44 and 45 positioned opposite each other and configured to move toward each other (either or both of the bars 44 and 45 may be moved) during the operation of the selective access system 10. Each of the bars 44 and 45 includes a heating element 46 positioned at the leading edge 47.

The severing bars 41 are configured to press against the sample assembly 20 from opposite sides of the sample assembly 20 during the operation of the selective access system 10. The severing bars 41 are configured to exert a force onto the sample assembly 20, while the heating elements 46 are heated, in order to sever the sample assembly 20 into a non-accessed portion 22 and an accessed portion 23. In particular, a plastic container holding the cryopreserved sample is squeezed so that opposing sides of the container contact each other and are sealed together to divide the container into two parts.

The severing bars 41 may be made from an insulating and non-conductive material, such as, for example, ceramic. Having severing bars 41 made from an insulating material (i.e., a poor conductor of heat) may allow the selective access system 10 to more easily thaw a narrow channel through the sample assembly 20, while only thawing a small portion (e.g., 2-5%) of the sample assembly 20. Having severing bars 41 made from a non-conductive material (i.e., a poor conductor of electricity) may allow the heating elements 46 to be located directly on the leading edges 47 of the severing bars 41, without posing a risk of short-circuiting the heating elements 46.

The compressor 42 is coupled to one or both severing bars 41 to provide a force to move one or both severing bars 41 towards the sample assembly 20, and to provide a force to press one or both severing bars 41 against the sample assembly 20, during operation of the selective access system 10. In the embodiment shown in FIG. 2, the compressor 42 is a pneumatic cylinder, and the compressor 42 is coupled to the upper bar 44, so that when the compressor 42 is actuated, the upper bar 44 moves downward toward the sample assembly 20. In other embodiments, the compressor 42 may be any other mechanism known in the art that is capable of moving the upper bar 44 and/or the lower bar 45 towards and away from the sample assembly 20, and that is capable of pushing the upper bar 44 and/or the lower bar 45 against the sample assembly 20 with sufficient force to maintain contact between the heating elements 46 and the sample assembly 20 during operation of the selective access system 10.

The compressor 42 may include a sensing switch that actuates when the leading edges 47 of the upper bar 44 and the lower bar 45 are within a desired distance of each other. In some embodiments, the compressor 42 may include a sensor that records the vertical displacement of the leading edge 47 of the upper bar 44 as it moves from an initial position, downward toward the leading edge 47 of the lower bar 45. Either such a sensing switch or such a sensor may be used to determine how much pressure to apply to the upper bar 44 and/or the lower bar 45 or what at temperature to set the heating elements 46. For example, when sensing switch included in the compressor 42 determines that the upper bar 44 and the lower bar 45 are within 10 mm (or any other user-determined distance boundary) of each other, the switch may energize an electrical circuit that may increase the temperature of the heating elements 46, in order to being the process of melting and fusing opposing portions of the plastic bag 21 to create a seal 24 that separates the non-accessed portion 22 from the accessed portion 23 of the sample assembly 20.

The compressor 42 may also include a sensor that records the force applied by the upper bar 44 and/or the lower bar 45 onto the sample assembly 20. The compressor 42 may receive instructions from the pressure controller 52 (for example, as programmed by a user) to maintain the force applied by the upper bar 44 and/or the lower bar 45 within a predetermined range, for example, to prevent cracking of the frozen sample assembly 20 during operation of the selective access system 10.

Each heating element 46 may be a narrow (e.g., approximately 1 mm wide, but 4 mm is more desirable to allow reliable partition of the portions after sealing) electrical resistive heating element that runs along the longitudinal axis of the leading edge 47, the leading edge 47 being, for example, 3-5 mm wide. In some embodiments, the heating elements 46 may be any width, for example, 0.5 mm, 2 mm, or as wide as the leading edge 47 of the severing bars 41 (e.g., 3-5 mm wide).

The heating elements 46 may be made from nickel chromium steel, for example, or the heating elements 46 may be made from any other heating element that can be temperature-controlled to the desired temperature range during operation of the selective access system 10. In an example embodiment, the heating elements 46 have a known electrical resistance that may be correlated with the absolute temperature of the heating element. Such a heating element 46 with a known electrical resistance may be capable of having its temperature carefully controlled by a user, via careful control of the electricity that is directed to flow through the heating element 46.

During operation of the selective access system 10, the heating elements 46 may be set to a series of specific temperatures to cause localized melting of frozen phases within the frozen sample assembly 20. The localized melting of the sample assembly 20 may be accomplished by the heating elements 46 by conduction of heat through the relatively thin plastic bag 21 into the frozen phases (e.g., the frozen biological material) inside of the sample assembly 20.

Figure 5:
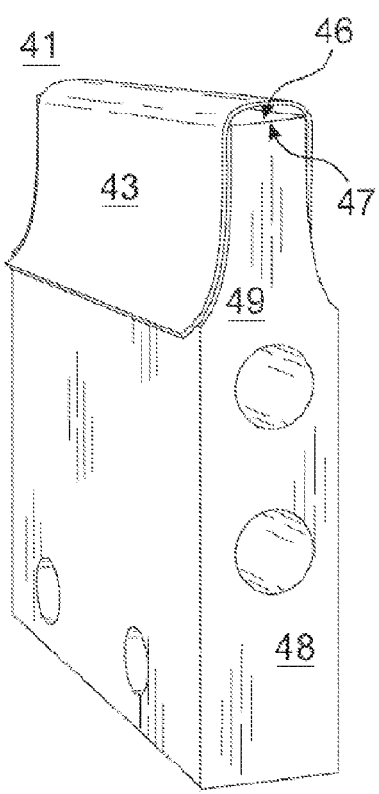
FIG. 5 is a side perspective view of one of the severing bars depicted in FIG. 2.

Referring now to FIG. 5, each of the upper bar 44 and the lower bar 45 are shaped with a narrow leading edge 47, a wide trailing portion 48 located opposite the leading edge 47, and a gradually widening transition portion 49 located between the leading edge 47 and the trailing portion 48. As shown in FIG. 5, each heating element 46 may be covered by a thin, heat-resistant, flexible cover 43. Each cover 43 may cover a respective heating element 46, thereby preventing molten materials (e.g., plastic from the plastic bag 21) from sticking to the heating elements 46 during operation of the selective access system 10. The cover 43 can be made of polymer material, such as any material described in association with the release layer of FIG. 9A.

The tapered shape and low-heat-transfer nature of the bars 44 and 45, along with the narrow width of the heating elements 46 compared to the width of the leading edge 47, may permit heat to be applied to the sample assembly 20 in a narrow strip, which may help to minimize thawing of the biological material inside the sample assembly 20 during operation of the selective access system 10. In an example embodiment, the heating elements 46 only produce enough heat energy to cause thawing of the biological material within the immediate vicinity of the advancing severing bars 41, for example, within a few millimeters of the heating elements 46.

The localized heat production of the heating elements 46, the tapered shape of the severing bars 41, and the low-heat-transfer nature of the material comprising the severing bars 41 may permit biological material inside the sample assembly 20, that is thawed during the operation of the selective access system 10, to flow back along the unheated portions (the transition portion 49 and the trailing portion 48) of the bars 44 and 45 and quickly refreeze.

The heat and pressure control system 50 includes a temperature controller 51 for controlling the temperature of the heating elements 46 and a pressure controller 52 for controlling the pressure supplied by the compressor 42. The temperature controller 51 is connected to the heating elements 46 (either directly connected to both eating elements 46, or directly connected to a first heating element 46 and connected to the second heating element 46 through the first heating element 46.

The temperature controller 51 may measure the electrical resistance of each heating element 46 to determine the temperature of each heating element 46 (via a correlation between the measured electrical resistance of each heating element 46 and the respective temperature of each heating element 46. Depending on the measured electrical resistance of each heating element 46, the temperature controller 51 may apply an electric current to one or both of the heating elements 46 to increase the temperature of the respective heating element 46, or the temperature controller 51 may discontinue the electric current being supplied to one or both of the heating elements 46 to reduce the temperature of the respective heating element 46. The ability of the temperature controller 51 to alternately measure electrical resistance and apply electric current to the heating elements 46 may provide a user the ability to control and change the temperature of the heating elements 46 during the operation of the selective access system 10. The temperature controller 51 may be programmed to set the temperature of each heating element 46 during the operation of the selective access system 10, or the temperature controller 51 may receive instructions to set the temperature of each heating element 46 via communication with a computer.

The pressure controller 52 is connected to the compressor 42. The pressure controller 52 may be programmed to set the force applied to the upper bar 44 and/or the lower bar 45 during the operation of the selective access system 10. The pressure controller 52 may be programmed to maintain the force applied to the upper bar 44 and/or the lower bar 45 within a predetermined range that may be set by the user. In some embodiments, the temperature controller 51 and the pressure controller 52 may be combined into a single component, for example, an electronic controller that can control the temperature of each heating element 46 and the pressure applied by the compressor 42.

The selective access system 10 may be used to isolate and sever the accessed portion 23 of the sample assembly 20 from the non-accessed portion 22 of the sample assembly 20. The method of isolating and severing the accessed portion 23 from the non-accessed portion 22 may include two processes: (i) a frozen phase melting process, and (ii) a plastic container sealing process.

The frozen phase melting process includes pressing the heating elements 46 against the sample assembly 20 until the portion of the sample assembly 20 that is located directly between the severing bars 41 melts and flows away from the heating elements 46 (the melted material later refreezes), so that the severing bars 41 reach a close enough distance to each other (e.g., 1 mm) so that the plastic container sealing process may begin.

To begin the frozen phase melting process, a user may cool the block enclosure 31 to a target temperature, for example, −196° C., by immersing the block enclosure 31 in liquid nitrogen for a sufficient time. The user may then place the sample assembly 20 inside the internal cavity 36 of the block enclosure 31, between the upper block portion 34 and the lower block portion 35, and the user may fasten the block enclosure 31 closed by tightening the connecting elements 37. The user may place the block enclosure 31 inside the block receiver 32, and the user may actuate the block positioning elements 33 so that the desired accessed portion 23 of the sample assembly 20 is positioned beyond a vertical plane defined by the leading edges 47 of the severing bars 41, such that the desired location of the seal 24 is intersected by the vertical plane defined by the leading edges 47 of the severing bars 41.

Next, the heat and pressure control system 50 may begin to heat the heating elements 46 to a desired initial temperature (e.g., between 50-100° C.) suitable for isolating and severing a portion of a particular cell sample or other biological material. The heat and pressure control system 50 may then begin to move one or both of the severing bars 41 towards the desired contact portion of the sample assembly 20. In the example shown in FIG. 2, for example, the upper bar 44 is moved downward by the compressor 42, while the lower bar 45 remains in a fixed position.

When the severing bars 41 contact the sample assembly 20, the compressor 42 may begin to force the severing bars 41 against the sample assembly 20, using an initial amount of force (e.g., between 5-25 lbs. per linear inch). As the severing bars 41 advance into the sample assembly 20, the force provided by the compressor 42 may be changed over time so that the force is sufficient to allow the severing bars 41 to maintain contact with the sample assembly 20 across substantially all of the portion of the plastic bag 21 that is anticipated to become part of the seal 24 (e.g., so that the heat is evenly applied across the anticipated seal 24). As the severing bars 41 advance into the sample assembly 20, the force provided by the compressor 42 may be changed over time so that the force increases from the initial force to a sealing force (i.e., the desired force at which the severing bars 41 form a seal in the plastic bag 21). A maximum force applied by the severing bars 41 against the sample assembly 20 may be selected by the user, for example, in order to prevent cracking or fracturing of the frozen phase cellular or biological material sample included in the sample assembly 20.

When the severing bars 41 contact the sample assembly 20, the heating elements 46 (which have been heated to the desired initial temperature) may begin to melt a small portion of the frozen phase material inside of the sample assembly 20 that is within a small distance of the heating elements 46 (e.g., 10 mm). As the severing bars 41 advance into the sample assembly 20, the temperature of the heating elements 46 may be changed over time so that the temperature of the heating elements 46 increases from the initial temperature (e.g., between 50-100° C.) to a sealing temperature (i.e., the desired temperature at which the severing bars 41 form a seal 24 in the plastic bag 21, for example, between 140-160° C.).

During the frozen phase melting process, the temperature of the heating elements 46 may be set within a range that is high enough to melt (i.e., change to a liquid phase) a portion of the frozen phase material that is within a small distance of the heating elements 46. The temperature of the heating elements 46 be set within a range that is low enough so that the plastic material in the plastic bag 21 does not begin to melt before the beginning of the plastic container sealing process (described below).

As the severing bars 41 advance into the sample assembly 20, the plastic material of the plastic bag 21 may stretch at the point of contact with the severing bars 41, and a depression (that will eventually be the location of the seal 24) may be formed in the frozen phase material inside the sample assembly 20 between the non-accessed portion 22 and the accessed portion 23. As the frozen phase material is melted (becoming liquid phase material) by the heating elements 46 at the leading edges 47 of the severing bars 41, the liquid phase material may flow away from the leading edges 47 of the severing bars 41 towards the transition portions 48 and the trailing portions 48 of the severing bars 41.

Because the severing bars 41 are made from a relatively low-heat-conducting material such as ceramic, and because of the tapered shape of the severing bars 41, the transition portions 49 and the trailing portions 48 of the severing bars 41 may be lower than the temperature of the leading edges 47, so that the temperature of the liquid phase material is gradually reduced as it flows further away from the leading edges 47 (and away from the heating elements 46) of the severing bars 41. Because the heating of the frozen phase material by the heating elements 46 may be localized over a relatively small area (e.g., 10 mm), the liquid phase material that travels away from the leading edges 47 along the transition portions 49 and the trailing portions 48 may quickly cool and refreeze, thereby preserving the protective effect of cryopreservation. In an example embodiment, approximately 2-5% of the frozen phase material included in the sample assembly 20 may be melted and refrozen during the operation of the selective access system 10.

As the severing bars 41 advance into the sample assembly 20, and the plastic material of the plastic bag 21 stretches at the point of contact with the severing bars 41, and a depression is formed in the frozen phase material inside the sample assembly 20, the block positioning elements 33 may push the block enclosure 31 and the sample assembly 20 away from the severing bars 41. This movement of the sample assembly 20 away from the severing bars 41 may help to maintain the position of the severing bars 41 relative to the depression that may be formed in the sample assembly 20 as the severing bars 41 advance into the sample assembly 20.

The frozen phase melting process may continue (e.g., for a few minutes) until the severing bars 41 penetrate into the sample assembly 20 to a sufficient degree that the severing bars 41 reach the desired separation distance from each other (e.g., 0.015-0.075 in.). A sensor that records the vertical displacement of one or both of the severing bars 41 or a sensing switch that is triggered when the severing bars 41 reach the desired separation switch may send a signal to the heat and pressure control system 50 that the frozen phase melting process has ended.

The plastic container sealing process includes increasing the temperature of the heating elements 46 and the pressure applied by the severing bars 41 against the plastic bag 21, so that opposite sides of the plastic bag 21 directly between the heating elements 46 melt and fuse to form a seal 24 that separates the accessed portion 23 from the non-accessed portion 22.

To begin the plastic container sealing process, the severing bars 41 may be positioned proximate either side of the plastic bag 21 at the location where the user desires to form a seal 24. At the beginning of the plastic container sealing process, all of the frozen phase material directly between the leading edges 47 of the severing bars 41 may have melted, flowed along the interior of the plastic bag 21 away from the leading edges 47, and refrozen at a location that is further away from the heating elements 46.

If the force being applied by the severing bars 41 against the plastic bag 21 has not already reached the desired sealing force, then the compressor 42 may increase the force applied by the severing bars 41 so that the desired sealing force is being applied against the plastic bag 21. Alternatively, if the force being applied by the severing bars 41 against the plastic bag 21 was gradually increased during the frozen phase melting process, the compressor 42 may already be applying the desired sealing force between the severing bars 41 and the plastic bag 21.

If the temperature of the heating elements 46 has not already reached the desired sealing temperature (e.g., between 140-160° C.), then the heat and pressure control system 50 may increase the temperature of the heating elements 46 so that the desired sealing temperature is being applied to the plastic bag 21 at the location of the desired seal 24. Alternatively, if the temperature of the heating elements 46 was gradually increased during the frozen phase melting process, the heating elements 46 may already be applying the desired sealing temperature to the plastic bag 21.

The desired sealing temperature may be selected such that the sealing temperature can heat the plastic bag 21 at the location of the desired seal 24 to a temperature that softens the plastic of the container, and the desired sealing force may be selected such that the severing bars 41 can press the two sides of the plastic bag 21 together, such that the heat and/or pressure at the location of the desired seal 24 may fuse the two sides of the plastic bag 21 together.

The desired sealing temperature, desired sealing force, and the duration of the plastic container sealing process may be chosen to be high enough to sufficiently seal the sides of the plastic bag 21 to create the seal 24. However, the desired sealing temperature, desired sealing force, and the duration of the plastic container sealing process may be chosen to be low enough to minimize the amount of heat added to the frozen phase material included in the sample assembly 20, thereby minimizing additional melting of the frozen phase material during the plastic container sealing process.

The plastic container sealing process may continue (e.g., for between 7-20 seconds) until the seal 24 has been created between the sides of the plastic bag 21. The heat and pressure control system 50 may cease the application of the sealing force and the production of heat at the heating elements 46, for example, when a signal is received that indicates that the leading edges 47 of the severing bars 41 have pressed towards each other to a desired predetermined minimum distance that is sufficient to create the seal 24 (using the desired sealing temperature). In some embodiments, a signal to end the plastic container sealing process may be sent to the heat and pressure control system 50 when a sensor that records the vertical displacement of one or both of the severing bars 41 (e.g., located within the compressor 42) or a sensing switch (e.g., as described above) indicates that the severing bars 41 have reached the desired separation distance.

In some embodiments, severing of the accessed portion 23 from the non-accessed portion 22 of the sample assembly 20 may be made easier for a user by the incorporation of pointed geometries on the leading edges 47 of the severing bars 41. For example, if a portion of the leading edges 47 at the heating elements 46 forms a relatively small surface area (e.g., approximately 1 mm wide) that extends from the rest of the leading edges 47 (e.g., a pointed geometry incorporated into each heating element 46 that protrudes approximately 1 mm away from the surface of the leading edges 47), then the seal 24 may include a thin line-shaped groove set into the fused sides of the plastic bag 21 that may permit easy separation of the accessed portion 23 from the non-accessed portion 22 by a user manually pulling (or cutting) the portions 22 and 23 apart from each other.

After the a frozen phase melting process and the plastic container sealing process have been completed, a user may return the stably frozen non-accessed portion 22 to a freezer or a container of liquid nitrogen. Also, a user may return the stably frozen accessed portion 23 to a freezer or a container or liquid nitrogen. Alternatively, the user may soon thaw the accessed portion 23 so that the user may, for example, expand ex vivo cord blood NK cells from the accessed portion 23 in advance of transplantation of the remaining non-accessed portion 22 of the same or other UCB unit or units.

Referring now to FIG. 7, a second embodiment selective access system 100 includes a sample assembly 120, a cooling system 130, a heat source 140, a heat source control system 150, a sealer 160, and a sterilizer 170. The sample assembly 120 includes a storage container 121, tubing 122, a collection container 123 and a sample 124. The sample 124 includes a frozen portion 125, a selected portion 126, and a thawed portion 127. The cooling system 130 includes a coolant reservoir 131, a storage tank 132, an inlet line 133, an outlet line 134, and insulation 135.

Second embodiment selective access system 100 was designed to thaw the selected portion 126 of the cryopreserved sample 124, which is available for use as the thawed portion 127, while the cooling system 130 keeps the frozen portion 125 in a stable frozen state.

The sample assembly 120 may include umbilical cord blood, for example, any of the various cell samples or biological material samples described above with reference to the sample assembly 20, or any other sample material for which a user may desire thawing of a selected portion 126 of the frozen sample 124. The sample assembly 120 may also contain plasma, serum antibodies, lymphocytes, or any other cellular or non-cellular material. The sample assembly 120 may contain a human sample, or it may contain an animal sample, a plant sample, a synthetic sample, or any frozen sample for which selective access is desired.

The storage container 121 is the container in which the sample 124 is stored before undergoing the selective thaw process. The storage container 121 may be a plastic bag that is commonly used to store umbilical cord blood or other samples 124 in a stable cryopreserved state. The tubing 122 is attached to one end of the storage container 121, and it is the outlet through which the sample 124 is removed. The collection container 123 may be a sterile plastic bag or other sterile receptacle, selectively coupled to the end of the tubing 122 that is not attached to the storage container 121, which is used to receive and store the thawed portion 127 after it achieves a liquid state. In other embodiments, the storage container 121, the tubing 122, and the collection container 123 may be different portions of a single bag or other container, wherein the selected portion 126 is thawed in one portion of the container and moved to another portion of the container after it becomes the thawed portion 127.

The sample 124 initially includes the frozen portion 125 and the selected portion 126. After thawing, the sample 124 includes the frozen portion 125 and the thawed aliquot portion 127. The frozen portion 125 is the portion of the sample 124 that is not thawed by the selective access system 100, and it may be approximately 90% of the sample 124. However, the frozen portion 125 may be any portion of the sample 124, e.g., 75%, 50%, or a lower percentage, so long as there is a significant enough sized frozen portion 125 to be thawed at another time. The exact portion of the sample 124 that remains as the frozen portion 125 after thawing may be determined by the particular requirements of the patient treatment protocol.

The mononuclear cell fraction thawed from umbilical cord blood units using conventional thawing methods (i.e., water baths) typically have at least 70% viability as assessed by trypan blue staining. The apparatus shown in FIG. 7 (and the apparatus shown in FIGS. 1-4) may maintain the integrity, sterility, and viability of the unthawed portion 125, so that when the portion 125 is subsequently thawed, the viability of mononuclear cells may be at least 50% of the post-thaw viability compared to the expected viability if the portion 125 had been thawed by a conventional method. The post-thaw viability of the subsequently-thawed portion 125 may be 50%, 75%, 90%, or 100% of the post-thaw viability compared to the expected viability if the portion 125 had been thawed by a conventional method. For example, when the portion 125 is subsequently thawed, the viability of mononuclear cells may be at least 70%, or 100% of the post-thaw viability compared to the expected viability if the portion 125 had been thawed by a conventional method.

The Selected portion 126 is the portion of the sample 124 that is thawed by the selective access system 100, and it may be approximately 10% of the sample 124. However, the selected portion 126 may be any portion of sample 124, e.g., 25%, 50%, or a higher percentage, so long as there is a significant enough sized selected portion 126 to allow the thawed portion 127 be used for the desired therapeutic purposes. During the thawing process, the selected portion 126 may transition from a frozen state to a liquid state. Once the selected portion 126 reaches a liquid state, it becomes the thawed portion 127, and it may be removed to the collection container 123, which may then be removed from the selective access system 100 for use in a therapeutic protocol.

The apparatus shown in FIG. 7 (and the apparatus shown in FIGS. 1-4) may maintain the integrity, sterility, and viability of the selectively thawed portion 126, so that the viability of mononuclear cells contained within the thawed portion 127 is at least 50% of the post-thaw viability compared to the expected viability if the thawed portion 127 had been thawed by a conventional method. The post-thaw viability of the thawed portion 127 may be 50%, 75%, 90%, or 100% of the post-thaw viability compared to the expected viability if the thawed portion 127 had been thawed by a conventional method. For example, viability of mononuclear cells contained within the thawed portion 127 may be at least 70%, or 100% of the post-thaw viability compared to the expected viability if the thawed portion 127 had been thawed by a conventional method.

For sample assemblies 20 or samples 124 that comprise other cell types, viability following thawing may be any amount, for example, between 50% and 95%, depending on the particular cell type. For example, when the sample assembly 20 or sample 124 includes an enriched CD34+ stem cell population, viability following thawing may be approximately 80-95%. With monocytes, the post-thaw viability may be approximately 50%. The skill level and experience of the laboratory that froze a particular UCB unit may affect the post-thaw viability percentage. For example, some UCB units that were frozen by more experienced centers may have a viability of thawed cells of greater than approximately 80%, while UCB units that were frozen by less experienced centers may have less than approximately 70% viability. It is believed that the post-thaw viability of a particular sample assembly 20 or sample 124, using the selective access system 10 or 100, may be at least 50% of the expected post-thaw viability if the sample had been thawed by a conventional thawing method (e.g., thawing the entire sample assembly 20 or sample 124 at a single time).

It should be noted that the selective access system 100 may be used multiple times on a single sample 124 to produce multiple thawed portions 127 on multiple occasions. For example, during a first selective thaw, 10% of the sample 124 may be thawed, producing a first thawed portion 127. During a second selective thaw, an additional 15% of the original volume of the sample 124 may be thawed, resulting in a second thawed portion 127. In this situation, 75% of the sample 124 may remain frozen as the frozen portion 125, while two separate thawed portions 127 were made available for use at separate times. The remaining 75% of the sample 124 may undergo selective thaw additional times, if a third or more than three thawed samples are required.

The cooling system 130 may keep the frozen portion 125 of the sample 124 in a stable frozen state during the operation of the selective access system 100. The cooling system 130 may use liquid nitrogen as the coolant, which may keep the frozen portion 125 of sample 124 at −196° C. In other embodiments, other coolants may be used, such as dry ice, which may keep frozen portion 125 at −76° C., or any circulating coolant may be used, or the insulation 135 may be used without a coolant. Any cooling system 130 may be used that is capable of keeping the frozen portion 125 at a low enough temperature, e.g., below −40° C., to keep it in a stable frozen state. In an example embodiment, the frozen portion 125 may remain frozen by heat transfer from the coolant reservoir 131, which may be filled with liquid nitrogen from the storage tank 132 via the inlet line 133. During the thawing process, any heat that is transferred to frozen portion 125 may transferred to the liquid nitrogen in the coolant reservoir 131. This heat may then be removed by permitting the slightly-warmed liquid nitrogen in the coolant reservoir 131 to migrate into the outlet line 134, where it may be discarded or re-cooled in the storage tank 132. In other embodiments, the slightly-warmed liquid nitrogen in coolant reservoir 131 may be pumped into the outlet line 134. After the liquid nitrogen is re-cooled in the storage tank 132, it may be re-circulated into the coolant reservoir 131 to remove additional excess energy from the thawing process.

The coolant reservoir 131 may be in the form of bladders, which may substantially surround the frozen portion 125 in the storage container 121 during the operation of the selective access system 100. The bladders that may comprise the coolant reservoir 131 may be made from a material that is suitable for storing liquid nitrogen or another low-temperature coolant medium while retaining some flexibility, e.g., a fluoro ethylene propylene (FEP) or a polyimide. In an example embodiment, the coolant reservoir 131 may surround approximately 90% of the volume of the frozen sample 124 in the storage container 121. In other embodiments, the coolant reservoir 131 may surround other percentages of the volume of the frozen sample 124, depending on how large of a thawed portion 127 relative to the total size of the frozen sample 124 is desired to be produced during the operation of the selective access system 100. The insulation 135 may completely surround the coolant reservoir 131, in order to minimize the heat transfer to the liquid nitrogen from the outside surface of the coolant reservoir 131, i.e., the surface not in contact with the storage container 121, which would otherwise be directly exposed to the ambient temperature of the room in which the selective access system 100 operates.

The combination of the coolant reservoir 131 and the insulation 135 within the cooling system 130 may take many other forms, such as using dry ice in Styrofoam insulation or other available combinations of coolants and insulation to keep the frozen portion 125 in a stably frozen state. In some embodiments, the cooling system 130 may also be a refrigeration unit capable of substantially surrounding the frozen portion 125 and keeping the frozen portion 125 in a stably frozen state. The exact configuration and components of the cooling system 130, the coolant reservoir 131, and the insulation 135 may be dictated by the temperature and heat transfer requirements for the particular frozen portion 125 of the sample 124.

The heat source 140 may provide the energy used to thaw the selected portion 126 of the sample 124. The heat source 140 may be a device that produces controlled infrared energy, which can be focused onto the selected portion 126 of the sample 124. The heat source 140 may be capable of focusing infrared energy onto the selected portion 126, such that the temperature of the selected portion 126 is gradually increased above the melting point of the sample 124. The heat source 140 may use any other technology to transfer energy to the selected portion 126, e.g., warm water, or ultrasonic energy, so long as the energy can be transferred to the selected portion 126 of the sample 124 in a controlled manner. The heat source 140 and the sealer 160 may be capable of applying simultaneous mechanical pressure and infrared thermal energy to the selected portion 126 of the frozen sample 124 to thaw the selected portion 126 and create a seal between the frozen portion 125 and the thawed portion 127.

The heat source control system 150 may include temperature probes for monitoring both the temperature of the frozen portion 125 and the selected portion 126 during the operation of the selective access system 100. The heat source control system 150 may also allow a user to control the operation of the heat source 140, which may be at least partially in response to the data produced by the temperature probes, and partially in response to variables input by the user, based on the properties of the particular sample 124 that is to be thawed. The heat source control system 150 also may allow a user to control the operation of the cooling system 130, for example, the rate of flow of liquid nitrogen into and out of the coolant reservoir 131 via the inlet line 133 and the outlet line 134. Different types of samples 124 may require thawing at a slower or faster rate, and to a higher or lower temperature, depending on the type of the sample 124 and the desired therapeutic use of the thawed portion 127. In some embodiments, the temperature probes in the heat source control system 150 may be used to crease a semi-automated feedback control system for temperature regulation of the frozen portion 125, the selected portion 126, and the thawed portion 127 of the sample 124.

The temperature of the frozen portion 125 may be monitored by the heat source control system 150, such that if the temperature of the frozen portion 125 is raised above a certain threshold, e.g., −40° C., the operation of the selective access system 100 may be adapted to prevent thawing of a portion of the sample 124 that exceeds the selected portion 126. The temperature of the frozen portion 125 may be maintained below the threshold temperature by decreasing the power emitted by the heat source 140 and/or increasing the heat transfer away from the frozen portion 125 by increasing the rate of replacement of the liquid nitrogen in the coolant reservoir 131.

The temperature of the selected portion 126 may be monitored by the heat source control system 150, such that the temperature of the selected portion 126 stays in a particular target zone, and it may be desired to set the rate of increase of temperature at a particular value. For example, the temperature of the selected portion 126 must eventually reach the melting point of the sample 124, such that thawing of the selected portion 126 can occur and change the selected portion 126 into the thawed portion 127. Depending on the type of the sample 124, the rate of temperature increase may need to be in a particular range, either rapid or slow thawing, such that damage to the sample 124 is minimized or prevented. The temperature and rate of temperature increase of the selected portion 126 may be increased or decreased by controlling the power emitted by the heat source 140.

In some embodiments, the temperature of the thawed portion 127 may be monitored by the temperature probes of the heat source control system 150, to prevent the thawed portion 127 from reaching a temperature that may cause damage to the thawed portion 127, depending on the type of sample 124.

The sealer 160 may be, for example, a radio frequency or ultrasonic based sealing device that is capable of sealing the tubing 122 that connects the storage container 121 with the collection container 123. After the operation of the selective access system 100 thaws the selected portion 126 to become the thawed portion 127, the thawed portion 127 may be moved to the collection container 123. The movement of the thawed portion 127 to the collection container 123 may be accomplished by the use of gravity, a mechanical pump, or any other means of creating a pressure differential between the storage container 121 and the collection container 123, such that the thawed portion 127 moves to the collection container 123.

After the thawed portion 127 reaches the collection container 123, the sealer 160 may seal tubing 122, for example, via radio frequency or ultrasonic welding or sealing, effectively separating the storage container 121 from the collection container 123. At this point, the storage container 121, which contains the frozen portion 125 of the sample 124 that was not thawed, may be returned to a freezer for later therapeutic use. The collection container 123 may be removed or decoupled from the tubing 122 and the storage container 121, so that the thawed portion 127 can be used for a therapeutic purpose, such as ex vivo expansion of the NK cells 2-4 weeks before transfusion of the entire UCB sample, including the frozen portion 125, to a patient. The sealer 160 may use radio frequency (RF) or ultrasonic technology to seal the tubing 122, but any other sealing technology may be used, so long as the process is sufficient to separate the collection container 123 from the storage container 121.

The sterilizer 170 may use irradiation by ultra-violet light, for example, to sterilize the sealed storage container 121 and/or the collection container 123 at the end of the operation of the selective access system 100. Other sterilization methods may be used, so long as they are capable of sterilizing the storage container 121 and/or the collection container 123 without causing excessive damage to the frozen portion 125 and/or the thawed portion 127 of the sample 124.

Referring now to FIG. 8A, a transplant protocol timeline 200 may include the steps of selective thaw or access 210, NK cell expansion 220, transplant conditioning 230, UCB and NK cell transplant 240, and GVHD prophylaxis 250.

The transplant protocol timeline 200 defines an example use of the first embodiment selective access system 10 and/or the second embodiment selective access system 100 to facilitate adoptive infusion of in vitro expanded cord blood NK cells following UCB transplantation to reduce GVHD and enhance graft-versus-tumor (GVT) effects. The beginning of the transplant protocol timeline 200 is approximately three weeks before time zero, which is defined by the time of the UCB and NK cell transplant 240. At three weeks before time zero, the selective thaw or access 210 is performed, in which either the selective access system 10 or 100 is used to generate an accessed portion 23 of a sample assembly 20 or a thawed portion 127 of a UCB unit sample 124 to obtain a small aliquot for the NK cell expansion 220. During the NK cell expansion 220, the NK cells from the accessed portion 23 or the thawed portion 127 of the UCB unit are isolated and in vitro expanded.

During the approximately three-week time period following the selective thaw or access 210 and the beginning of the NK cell expansion 220, the anticipated transplant patient may undergo transplant conditioning 230, which may be of a reduced intensity. At the end of the three-week time period following the selective thaw or access 210 and the beginning of the NK cell expansion 220, the UCB and NK cell transplant 240 takes place. During the UCB and NK cell transplant 240, the non-accessed portion 22 of the sample assembly 20 or the remaining frozen portion 125 of the UCB unit sample 124 and the in vitro expanded NK cells from the accessed portion 23 or the thawed portion 127 of the same UCB unit sample assembly 20 or sample 124 may be transplanted into the patient. The in vitro expanded UCB NK cells are adoptively infused at the time of UCB transplantation, which may reduce incidence of GVHD compared to UCB transplantation alone.

Following the UCB and NK cell transplant 240, the GVHD prophylaxis 250 is preferably performed for at least five weeks, in order to minimize the likelihood of the patient developing GVHD as a result of the UCB and NK cell transplant 240. It is important to note that the transplant protocol timeline 200 merely defines an example use of the selective access system 10 or 100, so the selective access system 10 or 100 may be used to support any protocol or other need for an accessed portion 23 of a sample assembly 20 or a selectively thawed portion 127 of a frozen sample 124.

Referring now to FIG. 8B, a transplant protocol timeline 300 may include the steps of selective thaw or access 310, T-cell expansion 320, transplant conditioning 330, UCB and T-cell transplant 340, and GVHD prophylaxis 350.

The transplant protocol timeline 300 defines an example use of the first embodiment selective access system 10 and/or the second embodiment selective access system 100 to facilitate adoptive infusion of ex vivo expanded viral-reactive T lymphocyte cells following UCB transplantation to reduce viral infection-related mortality. The beginning of the transplant protocol timeline 300 is approximately three weeks before time zero, which is defined by the time of the UCB and T-cell transplant 340. At three weeks before time zero, the selective thaw or access 310 is performed, in which either the selective access system 10 or 100 is used to generate an accessed portion 23 of a sample assembly 20 or a thawed portion 127 of a UCB unit sample 124 to obtain a small aliquot for the T-cell expansion 320. During the T-cell expansion 320, the virus-specific T-cells from the accessed portion 23 or the thawed portion 127 of the UCB unit are isolated and in vitro expanded.

During the approximately three-week time period following the selective thaw or access 310 and the beginning of the T-cell expansion 320, the anticipated transplant patient may undergo transplant conditioning 330, which may be of a reduced intensity. At the end of the three-week time period following the selective thaw or access 310 and the beginning of the T-cell expansion 320, the UCB and T-cell transplant 340 takes place. During the UCB and T-cell transplant 340, the non-accessed portion 22 of the sample assembly 20 or the remaining frozen portion 125 of the UCB unit sample 124 and the in vitro expanded T-cells from the accessed portion 23 or the thawed portion 127 of the same UCB unit sample assembly 20 or sample 124 may be transplanted into the patient. The in vitro expanded UCB T-cells are adoptively infused at the time of UCB transplantation, which may reduce incidence of viral infection-related mortality compared to UCB transplantation alone.

Following the UCB and T-cell transplant 340, the GVHD prophylaxis 350 is preferably performed for at least five weeks (e.g., seven weeks), in order to minimize the likelihood of the patient developing GVHD as a result of the UCB and T-cell transplant 340. It should be noted that the transplant protocol timeline 300 merely defines an example use of the selective access system 10 or 100, so the selective access system 10 or 100 may be used to support any protocol or other need for an accessed portion 23 of a sample assembly 20 or a selectively thawed portion 127 of a frozen sample 124.

Figure 9A:
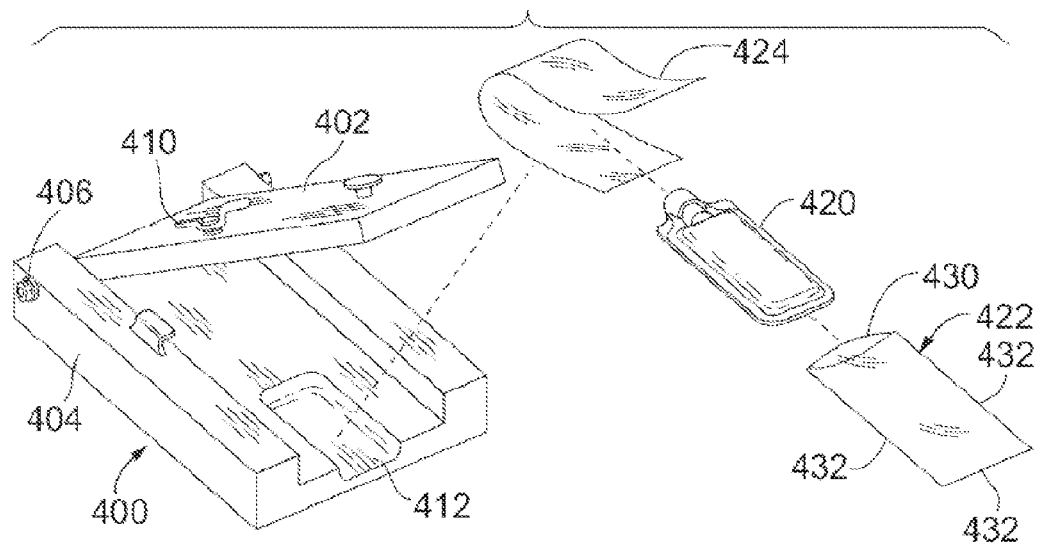
FIGS. 9A-9C are perspective views showing a container including a cryopreserved sample inserted into a patch-layer bag, with a layer of heat-resistant material (release film) placed as an outer layer, and the whole assembly placed into a cold block.

FIG. 9A shows another embodiment wherein a cold block 400 (also called the heat sink chamber) includes a hinged cover 402 attached to a base 404 using a hinge 406. The cold block can be made of aluminum or other metals (as described above) for maintaining cold temperatures after being cooled. The cover 402 is releasably lockable to the base 404 using a latch 410. A notch or cutout 412 is located at an end of the cold block opposite the hinge 406 and extends from an outer wall of the base 404 inwardly towards a center of the block. The notch is sized for receiving a sample assembly so that the cover 402 can be locked using hinge 406 without unduly squeezing the sample assembly. Additionally, the notch allows an external opening in the cold block through which the sample assembly can extend so that a portion of the sample assembly is retained in the cold block and a portion is retained external to the cold block. The sample assembly includes, in this embodiment, a container 420 containing the cryopreserved biological material within a single compartment, a patch-layer 422, and a release layer 424. The patch-layer can be made of plastic or any other material that melts at around the same temperature as the container 420 containing the cryopreserved material. As the patch layer melts, it welds to the container 420 and creates a patch for any tears in the container as it is being severed by the heating elements. The release layer 424 is a layer of heat-resistant material, such as a polymer material (e.g., polytetrafluoroethylene (PTFE), Perfluoroalkoxy (PFA), Fluorinated ethylene propylene (FEP), etc.), that can be positioned between the heating elements and the patch layer 422. The release layer can be thin enough to allow heat transfer to the container, but does not stick to the heating elements due to its higher melting point. Thus, the release layer protects the patch layer 422 and container 420 from being pulled apart as the heating elements are separated after the sealing process is completed.

The patch-layer 422 is shown as plastic patch-layer bag having three sealed ends 432 and an open end 430, in which the container 420 can be placed. The patch-layer bag has two advantages: first, as the heating elements melt the patch-layer, it provides additional material that flows into any tears in the container 420 to seal it; second, once the heating elements are removed, the patch-layer bag provides an extra sealed bag completely enclosing at least one part of the container 420 (which is separated into two parts) ensuring that the cryopreserved sample is not lost during the separation process. Although shown as a bag, the patch layer can be a ring around the container 420 in the location where the heating elements contact the container. Alternatively, the patch layer can be strips attached to the top and bottom of the container 420. Thus, the patch layer can take a variety of forms, but whatever form it takes, it desirably melts to seal and tears or cracks in the container.

The release layer 424 is shown as a single sheet large enough to overlap the sample assembly in the area of contact with the heating elements. Alternatively, the release layer can be a ring placed around the patch layer 422, two separate sheets or strips positioned on top of and on bottom of the patch layer 422, or the release layer can be placed on the surface of the heating elements, as previously described.

Figure 9B:
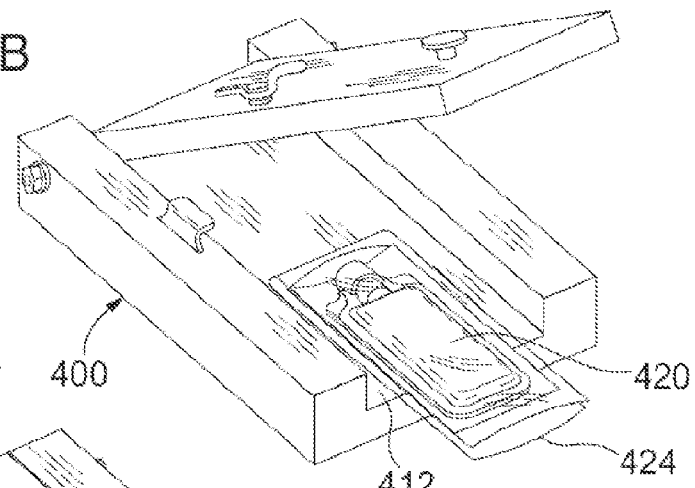
Figure 9C:
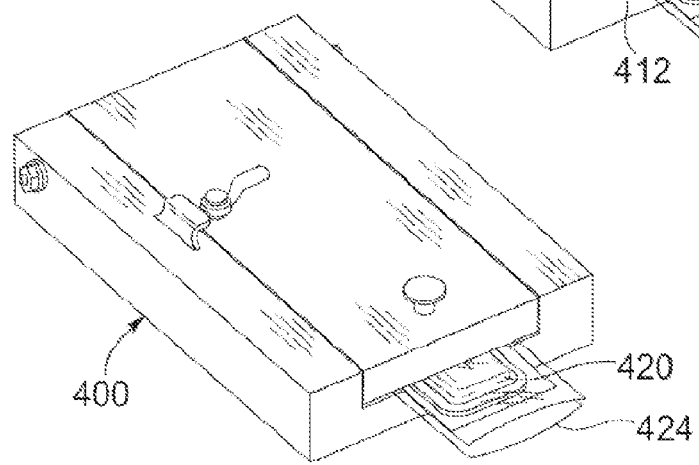

FIG. 9B shows the sample assembly including the container 420, patch layer 422 and release layer 424 placed into the notch 412 so that a portion of the sample assembly is positioned outside of the cold block 400 when the hinged cover 402 is in a closed position.

Figure 10:
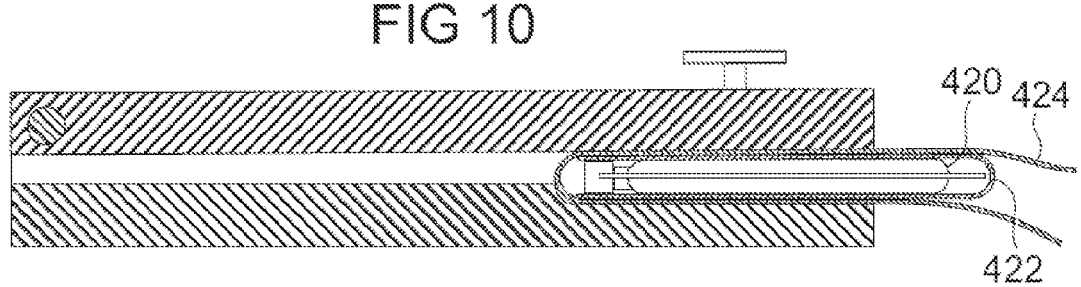
FIG. 10 shows a cross-sectional view of the assembly from FIG. 9 in the cold block.

FIG. 10 shows a cross-sectional view with three layers above the cyropreserved sample, and three layers below the cryopreserved sample. The layers include the top and bottom layers of the container 420, the top and bottom patch layers 422 and the top and bottom release layers 424. The heating elements sandwich these layers together, melting together the top and bottom layers of the container 420 and patch layers 422 to create a seal between the portion of the container 420 outside of the cold block and the portion within the cold block.

Figure 11A:
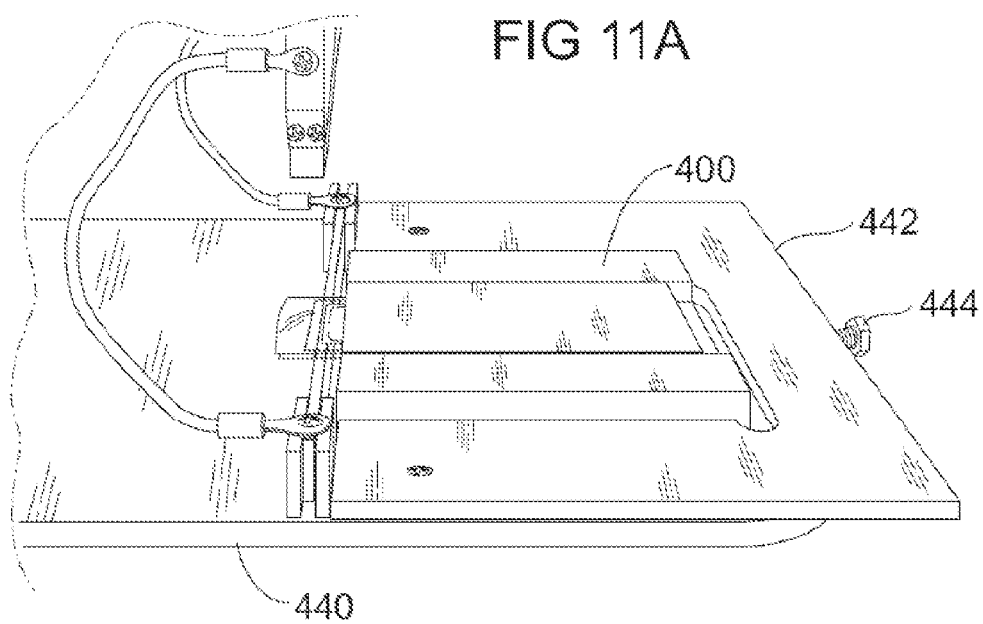
FIG. 11A shows the cold block of FIG. 10 positioned with the assembly between the severing bars.
Figure 11B:
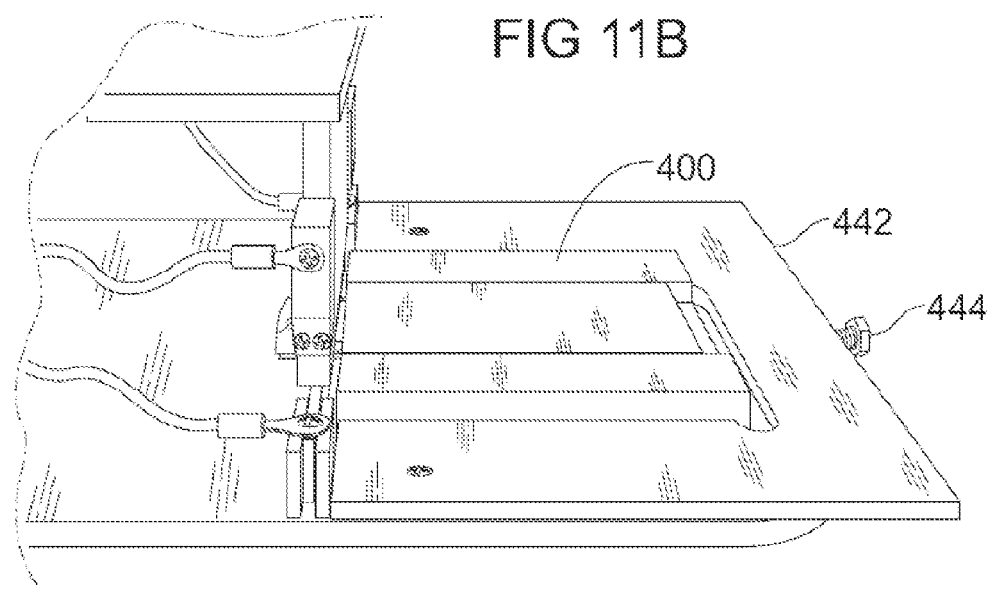

FIG. 11A shows the cold block 400 placed on a sealing table 440. The sealing table includes a jig 442 positioned thereon that is sized for receiving the cold block. The jig has one or more screws 444 extending there through for securing the position of the cold block as the heating elements clamp down onto the various layers of the container 420 containing the cryopreserved sample, the patch layer and the release layer. FIG. 11B shows the heating elements bearing down on the sample assembly. The result is a seal perpendicular to a longitudinal axis of the container, dividing the cryopreserved sample into two parts, which can then be cut with a scissor along the line of the seal. In some experiments performed, the container 420 was separated into a 5 ml portion and a 20 ml portion. Smaller containers have been separated into a 5 ml portion and a 1 ml portion.

It should be noted that the release layer and patch layer can be used in any of the embodiments described herein.

The foregoing description is provided for the purpose of explanation and is not to be construed as limiting the invention. While the invention has been described with reference to several embodiments or several methods, it is understood that the words which have been used herein are words of description and illustration, rather than words of limitation. Furthermore, although the invention has been described herein with reference to particular structure, methods, and embodiments, the invention is not intended to be limited to the particulars disclosed herein, as the invention extends to all structures, methods and uses that are within the scope of the appended claims. Those skilled in the relevant art, having the benefit of the teachings of this specification, may effect numerous modifications to the invention as described herein, and changes can be made without departing from the scope of the invention as defined by the appended claims. Furthermore, any features of one described embodiment can be applicable to the other embodiments described herein.

What is claimed:

1. A method for selectively accessing a portion of a sterile cryopreserved sample, the method comprising:
   placing a container having a cryopreserved sample therein in a heat sink chamber that surrounds a first portion of the container and maintains a second portion of the container outside of the heat sink chamber;
   creating a seal between the first and second portions using a heat source; and
   cutting along the seal to separate the first portion of the sample from the second portion.

2. The method of claim 1, wherein the heat source comprises two severing bars, each severing bar including a heating element.

3. The method of claim 2, wherein each severing bar is tapered from a narrow leading edge to a wider trailing portion.

4. The method of claim 2, wherein each heating element is covered by a heat resistant, flexible cover.

5. The method of claim 4, further comprising pressing the severing bars against the container until the seal is created.

6. The method of claim 2, further comprising controlling the temperature of each heating element with a temperature controller.

7. The method of claim 2, further comprising pressing the severing bars against the container adjacent to the second portion of the container.

8. The method of claim 1, further including placing a release film between the container and the heat source, the release film having a melting temperature higher than that of the container so that the heat source can melt the container without melting the release film.

9. The method of claim 8, further including placing a patch layer placed between the release film and the container, the patch layer being made of plastic and having a similar melting temperature to the container and further including filling any tears in the container using the patch layer.

10. The method of claim 1, wherein the cryopreserved sample comprises umbilical cord blood cells.

11. The method of claim 1, wherein the cryopreserved sample comprises lymphocytes.

12. The method of claim 1, wherein the cryopreserved sample comprises at least one of stem cells, red blood cells, white blood cells, modified cells, stromal cells, hybridoma cells, producer cells, pathogenic cells, epithelial cells, mesenchymal cells, sperm, embryos, biological cell parts, virus samples, rickettsial cells, vaccine materials, antigenic materials, cyotokines, and hormones.

* * * * *